US012685679B2

(12) United States Patent
Thibert et al.

(10) Patent No.: US 12,685,679 B2
(45) Date of Patent: Jul. 21, 2026

(54) REUSABLE SWIMWEAR GARMENT

(71) Applicant: Aquadini LLC, Austin, TX (US)

(72) Inventors: Diane Mary Thibert, Austin, TX (US); Nina Georgieva Sadauskas, Austin, TX (US)

(73) Assignee: Aquadini LLC, Austin, TX (US)

( * ) Notice: Subject to any disclaimer, the term of this patent is extended or adjusted under 35 U.S.C. 154(b) by 356 days.

(21) Appl. No.: 18/467,528

(22) Filed: Sep. 14, 2023

(65) Prior Publication Data

US 2024/0082072 A1     Mar. 14, 2024

Related U.S. Application Data

(60) Provisional application No. 63/406,604, filed on Sep. 14, 2022.

(51) Int. Cl.
*A61F 13/496*     (2006.01)
*A61F 13/15*     (2006.01)

(52) U.S. Cl.
CPC ...... *A61F 13/496* (2013.01); *A61F 13/15203* (2013.01); *A61F 2013/15195* (2013.01); *A61F 2013/15487* (2013.01)

(58) Field of Classification Search
CPC .......... A61F 13/505; A61F 2013/15195; A61F 13/49413; A61F 2013/4951; A61F 13/513; A61F 13/5116; A61F 13/4942
See application file for complete search history.

(56) References Cited

U.S. PATENT DOCUMENTS

| | | | | |
|---|---|---|---|---|
| 5,562,646 | A | * | 10/1996 | Goldman ................ A61L 15/42 |
| | | | | 428/339 |
| 5,643,653 | A | * | 7/1997 | Griesbach, III ......... D04H 1/54 |
| | | | | 604/370 |
| 5,669,598 | A | * | 9/1997 | Ticey ........................ F16F 1/32 |
| | | | | 425/410 |
| 6,822,136 | B1 | * | 11/2004 | Niemeyer ......... A61F 13/15203 |
| | | | | 604/378 |
| 7,678,094 | B1 | | 3/2010 | Cannon et al. |
| 2004/0127867 | A1 | * | 7/2004 | Odorzynski .......... A61F 13/505 |
| | | | | 604/359 |
| 2006/0116656 | A1 | * | 6/2006 | Hendren ............... A61F 13/565 |
| | | | | 604/396 |
| 2006/0122572 | A1 | * | 6/2006 | Suarez .............. A61F 13/53704 |
| | | | | 604/385.101 |

(Continued)

*Primary Examiner* — Michele Kidwell

(57)     ABSTRACT

Disclosed herein is a reusable swim garment capable of containing excreted human waste. The swim garment may comprise a swim brief and/or shell. The swim garment may provide level(s) of protection for containing excreted human waste, helping reduce or eliminate swimming facility closures and providing comfort to both the user and other occupants in the swimming facility. The plurality of levels of protection are provided by two or more of: safety stitches in one or more elastic bands (e.g., leg-receiving elastic bands, torso-receiving elastic band), grippers to create a seal at the user's waist and/or legs, fasteners used to temporarily attach or remove the swim garment to or from the user, or a containment insert. The containment insert may comprise layer(s) that absorb the human waste, confine human waste, or prevent or reduce exchange of liquids between the swim garment and the swimming environment.

19 Claims, 13 Drawing Sheets

(56) References Cited

U.S. PATENT DOCUMENTS

| | | | | |
|---|---|---|---|---|
| 2008/0103471 A1* | 5/2008 | LaVon | .................. | A61F 13/505 |
| | | | | 604/385.19 |
| 2019/0117471 A1* | 4/2019 | Brownlee | ......... | A61F 13/49017 |

* cited by examiner

210

211

205

207

200

238

112

250

410

412

414A

416

414B

430

REUSABLE SWIMWEAR GARMENT

CROSS-REFERENCE TO RELATED APPLICATION

This application claims the benefit of U.S. Provisional Application No. 63/406,604, filed Sep. 14, 2022, the entire contents of which are hereby incorporated by reference herein.

FIELD OF THE DISCLOSURE

This disclosure relates generally to a reusable swimwear garment, and more specifically, a reusable garment that contains human waste while swimming.

BACKGROUND OF THE DISCLOSURE

Traditional swimwear garments cover parts of the human body, but may not be effective at containing excreted human waste such as urine, feces, sweat, or blood. The excreted human waste may migrate outside of the swimwear garment into a swimming environment such as a swimming pool, lake, hot tub, bathtub, ocean, etc. This migration may lead to contamination of a swimming environment and closure of the swimming facility. Contaminating of the swimming environment may jeopardize the health of others, causing illnesses due to a virus, bacteria, or the like. The closure of a swimming pool may be costly in terms of both time and money. This may be particularly problematic when children are, e.g., swimming in a swimming pool. Traditional swim diapers are ineffective at completely containing excreted human waste; some only absorb liquids. Further, traditional swim diapers may become bulky when a child excretes human waste. A bulky swim diaper is not only uncomfortable, but may also restrict or weigh a child down. There are currently 320,000 drownings every year worldwide, and one of the causes is unintentional injury-related death of a child aged 5 years old or younger. 23% of child drownings occur during a family gathering near a swimming facility. Restricting or weighing a child down with a bulky swim diaper is unsafe and may prevent the child from being able to move freely, making it harder for the child to swim. Additionally, traditional swim diapers have a limited lifetime when reused. Washing traditional swim diapers causes deterioration in the quality and already-limited effectiveness in containing excreted human waste.

What is needed is a swim garment that completely contains excreted human waste when used in an aquatic environment. What is also needed is a swim garment that absorbs and contains excreted human waste such that it does not become uncomfortable, bulky, or weigh down the user. What is also needed is a swim garment that is reusable such that washing it does not cause deterioration in its quality and effectiveness.

SUMMARY OF THE DISCLOSURE

A containment insert for containing excreted human waste is disclosed. In some embodiments, the containment insert comprises: a filter layer that filters out solid human waste; an absorbent layer that absorbs liquid human waste; a confinement layer comprising one or more features for confining the solid human waste; and one or more waterproof layers that prevent or reduce liquids from penetrating through the containment insert. Additionally or alternatively, in some embodiments, the containment insert further comprises: an outer portion, an elevated portion, and an inner portion, wherein the one or more features are located in the elevated portion. Additionally or alternatively, in some embodiments, a thickness of the outer portion is between 2-5 mm; a thickness of the elevated portion is between 10-15 mm; or a thickness of the inner portion is between 4-7 mm, the containment insert further comprising a filter layer that filters out solid human waste, an absorbent layer that absorbs liquid human waste, a confinement layer comprising one or more features for confining the solid human waste, and one or more waterproof layers that prevent or reduce liquids from penetrating through the containment insert. Additionally or alternatively, in some embodiments, the containment insert further comprises: a front portion and a back portion, wherein a width of the front portion is less than a width of a back portion. Additionally or alternatively, in some embodiments, the filter layer is located on one side of the absorbent layer, and the absorbent layer is located between the filter layer and at least one of the one or more waterproof layers. Additionally or alternatively, in some embodiments, at least one of the one or more waterproof layers is located between the absorbent layer and the confinement layer. Additionally or alternatively, in some embodiments, at least one of the one or more waterproof layers is located on one side of the confinement layer, and another of the one or more waterproof layers is located between the absorbent layer and the confinement layer. Additionally or alternatively, in some embodiments, the filter layer allows some of the liquid human waste to pass through. Additionally or alternatively, in some embodiments, the filter layer comprises a perforated mesh fabric, a knitted hole fabric, rayon, tree cellulose, or a combination thereof. Additionally or alternatively, in some embodiments, a thickness of the filter layer is the same throughout an outer portion, an elevated portion, and an inner portion of the containment insert. Additionally or alternatively, in some embodiments, the absorbent layer comprises a French terry fabric, a hydrophilic foam or fabric, a Looped terry fabric, or a combination thereof. Additionally or alternatively, in some embodiments, the absorbent layer is located at an inner portion of the containment insert. Additionally or alternatively, in some embodiments, at least one of the one or more waterproof layers comprises a coated nylon fabric or a polyurethane film. Additionally or alternatively, in some embodiments, the confinement layer comprises a hydrophobic foam or fabric. Additionally or alternatively, in some embodiments, the confinement layer comprises a resilient foam fabric with properties that enhance moisture absorption and containment, providing improved performance in managing excreted human waste. Additionally or alternatively, in some embodiments, the one or more features comprise a valley formed from one or more elevated portions surrounding an inner portion, wherein the confinement layer at the inner portion is thinner than the confinement layer at the one or more elevated portions. Additionally or alternatively, in some embodiments, the confinement layer at an outer portion of the containment insert is thicker than the confinement layer at an inner portion of the containment insert. Additionally or alternatively, in some embodiments, a thickness of at least one of the one or more waterproof layers is the same throughout an outer portion, an elevated portion, and an inner portion of the containment insert. Additionally or alternatively, in some embodiments, at least one of the one or more waterproof layers comprises a coated nylon fabric or polyurethane film. Additionally or alternatively, in some embodiments, the containment insert is included or integrated into a swim brief. Additionally or alternatively, in some embodiments, the swim brief comprises an outer layer and an inner layer, wherein the outer layer and the inner layer cover front, back, and side portions of the swim brief. Additionally or alternatively, in some embodiments, the swim brief comprises an outer layer and an inner layer and one or more of: the outer layer or the inner layer cover a crotch portion of the swim brief. Additionally or alternatively, in some embodiments, the swim brief comprises an outer layer, the outer layer comprising a waterproof material. Additionally or alternatively, in some embodiments, the swim brief comprises an outer layer, the outer layer comprising a decorative design. Additionally or alternatively, in some embodiments, the swim brief comprises an inner layer, the inner layer comprising a breathable wick-away fabric. Additionally or alternatively, in some embodiments, the swim brief comprises an inner layer and sidewall barriers, the sidewall barriers surrounding edges of the containment insert and attached to the inner layer. Additionally or alternatively, in some embodiments, the swim brief comprises a fastener, wherein the fastener comprises a waterproof zipper. Additionally or alternatively, in some embodiments, one or more of: a torso-receiving elastic band or leg-receiving elastic bands of the swim brief comprise an inner layer of the swim brief, an elastic band, and an outer layer of the swim brief. Additionally or alternatively, in some embodiments, a deodorizing element is included to neutralize odors. Additionally or alternatively, in some embodiments, the containment insert is adapted for use in environments other than swimwear, including diapers, pads, or other waste-containment garments. Additionally or alternatively, in some embodiments, one or more of: a torso-receiving elastic band or leg-receiving elastic bands of the swim brief comprise a plurality of rows of stitching. Additionally or alternatively, in some embodiments, one or more of: a torso-receiving elastic band or leg-receiving elastic bands of the swim brief comprise an overlock edge. Additionally or alternatively, in some embodiments, one or more of: a torso-receiving elastic band or leg-receiving elastic bands of the swim brief comprise a gripper. Additionally or alternatively, in some embodiments, the swim brief provides a plurality of levels of protection for containing the solid human waste or the liquid human waste. Additionally or alternatively, in some embodiments, the plurality of levels of protection are provided by two or more of: safety stitches in one or more elastic bands of the swim brief, grippers that create a seal at a waist or legs of a user, or fasteners that temporarily attach or remove the swim brief to or from the user.

A swim garment is disclosed. The swim garment comprises: a swim brief configured to cover a bottom body part of a user, the swim brief comprising a containment insert, the containment insert comprises: a filter layer that filters out solid human waste; an absorbent layer that absorbs liquid human waste; and a confinement layer comprising one or more features for confining the solid human waste; and a shell configured to cover a non-bottom body part of the user. Additionally or alternatively, in some embodiments, the swim brief has an adjustable waistband for a customizable fit, wherein the adjustable waistband includes one or more fasteners for easy removal and adjustment of the swim brief. Additionally or alternatively, in some embodiments, the shell comprises a bottom portion that extends below leg-receiving elastic bands of the swim brief. Additionally or alternatively, the swim brief comprises leg-receiving elastic bands that create a secure seal around a user's legs. Additionally or alternatively, in some embodiments, the shell attaches to a torso-receiving elastic band of the swim brief. Additionally or alternatively, in some embodiments, the shell comprises a top portion that extends above a torso-receiving elastic band of the swim brief. Additionally or alternatively, in some embodiments, the shell comprises sleeves. Additionally or alternatively, in some embodiments, the shell is configured to cover the bottom body part of the user. Additionally or alternatively, in some embodiments, the swim brief is configured for use by users of all ages. Additionally or alternatively, in some embodiments, an outer layer of the swim garment comprises at least a part of an outer layer of the swim brief or the shell. Additionally or alternatively, in some embodiments, an inner layer of the swim garment comprises at least a part of an inner layer of the swim brief or the shell. Additionally or alternatively, in some embodiments, the containment insert comprises: an outer portion, an elevated portion, and an inner portion, wherein the one or more features are located in the elevated portion. Additionally or alternatively, in some embodiments, a thickness of the outer portion is between 2-5 mm; a thickness of the elevated portion is between 10-15 mm; or a thickness of the inner portion is between 4-8 mm. Additionally or alternatively, in some embodiments, the containment insert comprises: a front portion and a back portion, wherein a width of the front portion is less than a width of a back portion. Additionally or alternatively, in some embodiments, the swim garment further comprises: one or more waterproof layers that prevent or reduce liquids from penetrating through the containment insert. Additionally or alternatively, in some embodiments, at least one of the one or more waterproof layers is included in the swim brief. Additionally or alternatively, in some embodiments, at least one of the one or more waterproof layers is included in the shell. Additionally or alternatively, in some embodiments, at least one of the one or more waterproof layers is located between the absorbent layer and the confinement layer of the containment insert. Additionally or alternatively, in some embodiments, at least one of the one or more waterproof layers is located on one side of the confinement layer of the containment insert, and another of the one or more waterproof layers is located between the absorbent layer of the containment insert and the confinement layer. Additionally or alternatively, in some embodiments, the filter layer of the containment insert is located on one side of the absorbent layer of the containment insert, and the absorbent layer is located between the filter layer and at least one of the one or more waterproof layers. Additionally or alternatively, in some embodiments, at least one of the one or more waterproof layers comprises a coated nylon fabric or polyurethane film. Additionally or alternatively, in some embodiments, a thickness of at least one of the one or more waterproof layers is the same throughout an outer portion, an elevated portion, and an inner portion of the containment insert. Additionally or alternatively, in some embodiments, at least one of the one or more waterproof layers comprises a coated nylon fabric or polyurethane film. Additionally or alternatively, in some embodiments, the filter layer of the containment insert allows some of the liquid human waste to pass through. Additionally or alternatively, in some embodiments, the filter layer of the containment insert comprises a perforated mesh fabric, a knitted hole fabric, rayon, tree cellulose, or a combination thereof. Additionally or alternatively, in some embodiments, a thickness of the filter layer of the containment insert is the same throughout an outer portion, an elevated portion, and an inner portion of the containment insert. Additionally or alternatively, in some embodiments, the absorbent layer of the containment insert comprises a hydrophilic foam or fabric, a Looped Terry fabric, a French terry fabric, or a combination thereof. Additionally or alternatively, in some embodiments, the absorbent layer of the containment insert is located at an inner portion of the containment insert. Additionally or alternatively, in some embodiments, the confinement layer of the containment insert comprises a hydrophobic foam or fabric. Additionally or alternatively, in some embodiments, the one or more features of the containment insert comprise a valley formed from one or more elevated portions surrounding an inner portion, wherein the confinement layer of the containment insert at the inner portion is thinner than the confinement layer at the one or more elevated portions. Additionally or alternatively, in some embodiments, the confinement layer at an outer portion of the containment insert is thicker than the confinement layer at an inner portion of the containment insert. Additionally or alternatively, in some embodiments, the containment insert further comprises a moisture-wicking layer disposed adjacent to the absorbent layer, the moisture-wicking layer is configured to transport liquid away from the absorbent layer. Additionally or alternatively, in some embodiments, the one or more waterproof layers are impermeable to liquids while allowing airflow to maintain comfort. Additionally or alternatively, in some embodiments, the containment insert further comprises an adhesive backing for secure attachment to an inner surface of a swim brief.

DETAILED DESCRIPTION

Figure 1A:
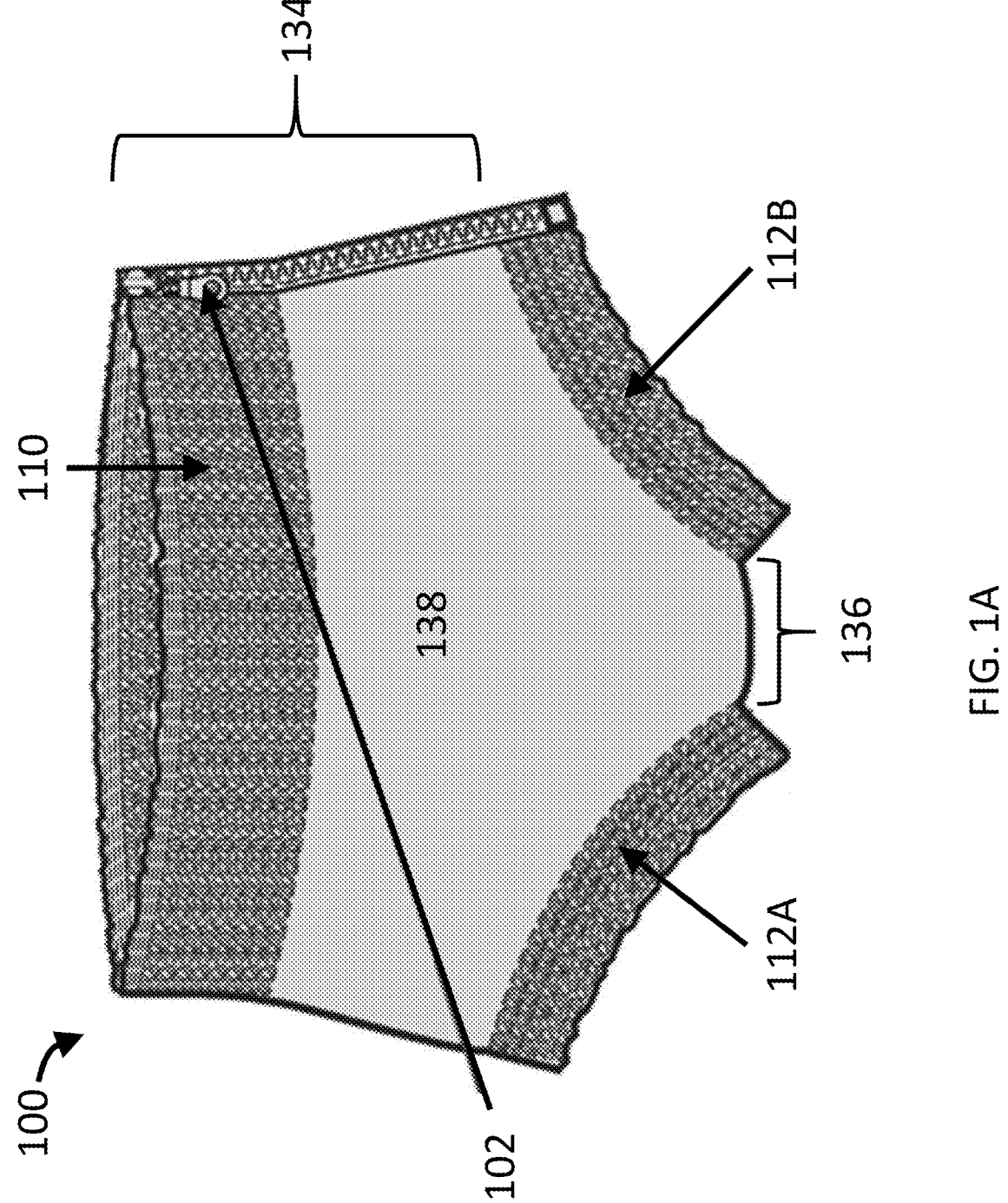
FIGS. 1A and 1B illustrate front and back views, respectively, of an example swim brief, according to some embodiments.

Disclosed herein is a reusable swim garment and methods of use and manufacture thereof. The swim garment may be capable of containing excreted human waste, while also being comfortable and reusable. The swim garment may comprise a swim brief and/or shell. The swim garment may allow the user to move freely (e.g., during swim lessons) without being restricted or weighed down due to the excreted human waste. The swim garment may provide a plurality of levels of protection for containing excreted human waste, helping reduce or eliminate swimming facility closures and providing comfort to both the user and other occupants in the swimming facility. The plurality of levels of protection are provided by two or more of: safety stitches in one or more elastic bands (e.g., leg-receiving elastic bands, torso-receiving elastic band), grippers to create a seal at the user's waist and/or legs, fasteners used to temporarily attach or remove the swim garment to or from the user, one or more layers that absorb the human waste, one or more layers that confine human waste, or one or more layers that prevent or reduce exchange of liquids between the swim garment and the swimming environment. Further, the swim garment may be capable of being used by users of all ages.

The following description is presented to enable a person of ordinary skill in the art to make and use various embodiments. Descriptions of specific devices, techniques, and applications are provided only as examples. These examples are being provided solely to add context and aid in the understanding of the described examples. It will thus be apparent to a person of ordinary skill in the art that the described examples may be practiced without some or all of the specific details. Other applications are possible, such that the following examples should not be taken as limiting. Various modifications in the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Various techniques and process flow steps will be described in detail with reference to examples as illustrated in the accompanying drawings. In the following description, numerous specific details are set forth in order to provide a thorough understanding of one or more aspects and/or features described or referenced herein. It will be apparent, however, to a person of ordinary skill in the art, that one or more aspects and/or features described or referenced herein may be practiced without some or all of these specific details. In other instances, well-known process steps and/or structures have not been described in detail in order to not obscure some of the aspects and/or features described or referenced herein.

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combination of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Figure 1B:
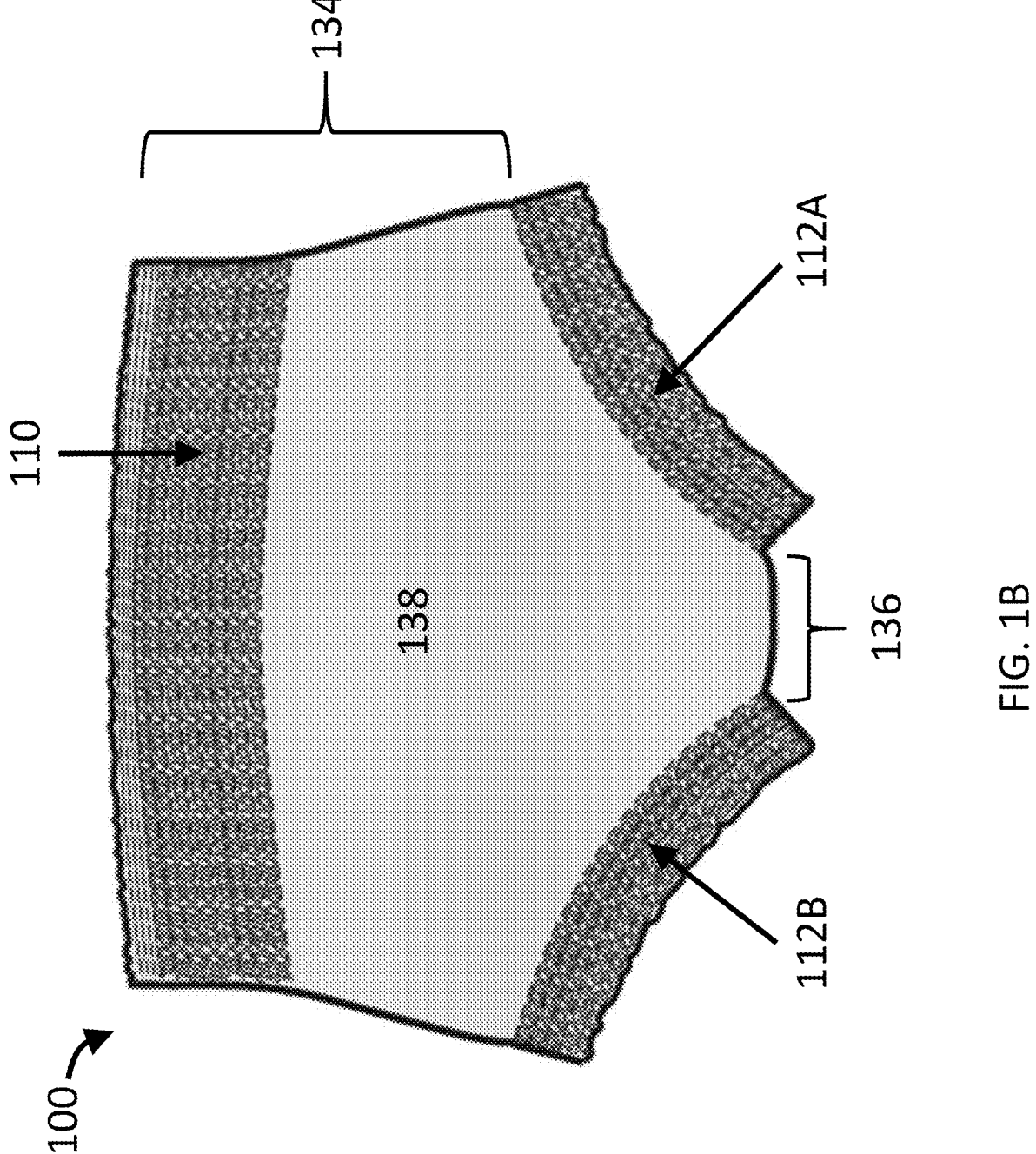

FIGS. 1A and 1B illustrate front and back views, respectively, of an example swim brief, according to some embodiments. These figures illustrate an outer layer 138 of the swim brief 100. Swim brief 100 may comprise a torso portion 134 with an elastic band 110 located at a top end and elastic bands 112A and 112B located at the bottom end. The elastic band 110 may form a torso-receiving opening, and each elastic band 112A or 112B may form a leg-receiving opening. The swim brief 100 may comprise a crotch portion 136 located between the leg-receiving elastic bands 112A and 112B. Embodiments of the disclosure include the swim brief 100 being a swim garment.

The torso-receiving elastic band 110 may be located along the user's torso area when the swim brief 100 is worn. For example, the torso-receiving elastic band 110 may be located proximate to the user's belly button (e.g., covering at least a part of the user's torso) when the swim brief 100 is worn. The leg-receiving elastic bands 112A and 112B may be located at the top of the user's legs when the swim brief 100 is worn. In some embodiments, the leg-receiving elastic bands 112A and 112B may extend (e.g., 1-2 inches) below the top of the user's legs. When worn, the front portion of the swim brief 100 is configured to cover at least part of the user's waist, the back portion is configured to cover at least part of the user's buttocks, and the side portions are configured to cover at least part of the user's hips.

The swim brief 100 may comprise an outer layer 138, which may be located furthest away from the user's skin compared to the other layers of the swim brief 100 when worn. At least one outer layer 138 may extend from the torso receiving opening to both leg-receiving openings, covering the front, back, and side portions. In some embodiments, the outer layer 138 may cover the crotch portion 136. Alternatively, a containment insert 130 may cover the crotch portion, and edges of the outer layer 138 may attach to edges of the containment insert 130. The outer layer 138 may be adhered (e.g., sewn) at the edges of the torso-receiving band 110 and leg-receiving openings 112A and 112B. In some embodiments, the outer layer 138 may be formed from a plurality of portions (e.g., a front portion and a back portion) of fabric that are stitched together at one or more seams (e.g., crotch seam, side seams, back seam, front seam, etc.).

The outer layer 138 may be configured to prevent or reduce external liquids, such as swimming facility water, from reaching or being absorbed by the other layers (e.g., intermediate layer(s) and/or inner layer) of the swim brief 100. One or more of: the outer layer 138, the torso-receiving elastic band 110, and the leg-receiving elastic bands 112A, and 112B, minimize the exchange of liquids, such as urine and swimming pool water, between the inside and outside of the swim brief 100. The elastic bands of the present disclosure may include any type of band that creates a snug closure.

In some embodiments, at least one outer layer may comprise a waterproof material including, but not limited to, a polyurethane film fabric or a coated woven nylon fabric such as thermoplastic polyurethane (TPU), polyurethane laminate (PUL), extra-long staple (ELS cotton), neoprene, rubber, or the like. In some embodiments, the outer layer 138 may comprise a 1-ply swimwear fabric. For example, the fabric may be an olefin-based fabric. In some embodiments, the outer layer 138 may comprise a fabric that is made from discarded and/or recycled nylon or polyurethane film products.

One or more fabrics used in the swim garment may be durable, while also being capable of being stretched to allow the user to be comfortable while wearing the swim garment. In some embodiments, one or more fabrics may have excellent resistance against heat, liquids, and/or ultraviolet rays. Example liquids include chlorine, salt water, suntan creams, sweat, and other human bodily fluids. The fabric(s) used in the swim garment may be a light to medium fabric, breathable, and moisture-wicking. In some embodiments, the swim garment may comprise one or more fabrics that are non-iron and wrinkle free after being laundered or used as a swim garment. As discussed in more detail below, the swim garment may comprise washable, iron- and wrinkle-free, and durable fabrics that allow the user to launder and reuse the swim garment with convenience. The swim garment may be capable of withstanding laundering conditions (e.g., immersed in water that is 140° F. or hotter) and subsequently returning to conditions substantially similar to the original conditions after being laundered.

In some embodiments, at least one of the outer layers 138 comprises a decorative fabric layer including one or more decorative designs. The decorative fabric layer may be located anywhere on the swim garment. For example, the decorative fabric layer may extend from the torso-receiving opening and both leg-receiving openings. In some embodiments, the decorative fabric layer may only be attached at one of the openings (e.g., torso-receiving opening, neck-receiving opening, etc.).

The decorative fabric visible layer can include any type of fabric; non-limiting examples include a nylon or polyurethane film having a printed decorative design. In some embodiments, the outer layers of the swim garment may comprise a waterproof layer and a decorative fabric layer. The decorative fabric layer may be at least partially transparent such that both the decorative fabric layer and the waterproof layer may be visible when looking at the outer layer of the swim garment. In some embodiments, a decorative design may be printed on the waterproof layer.

Figure 1C:
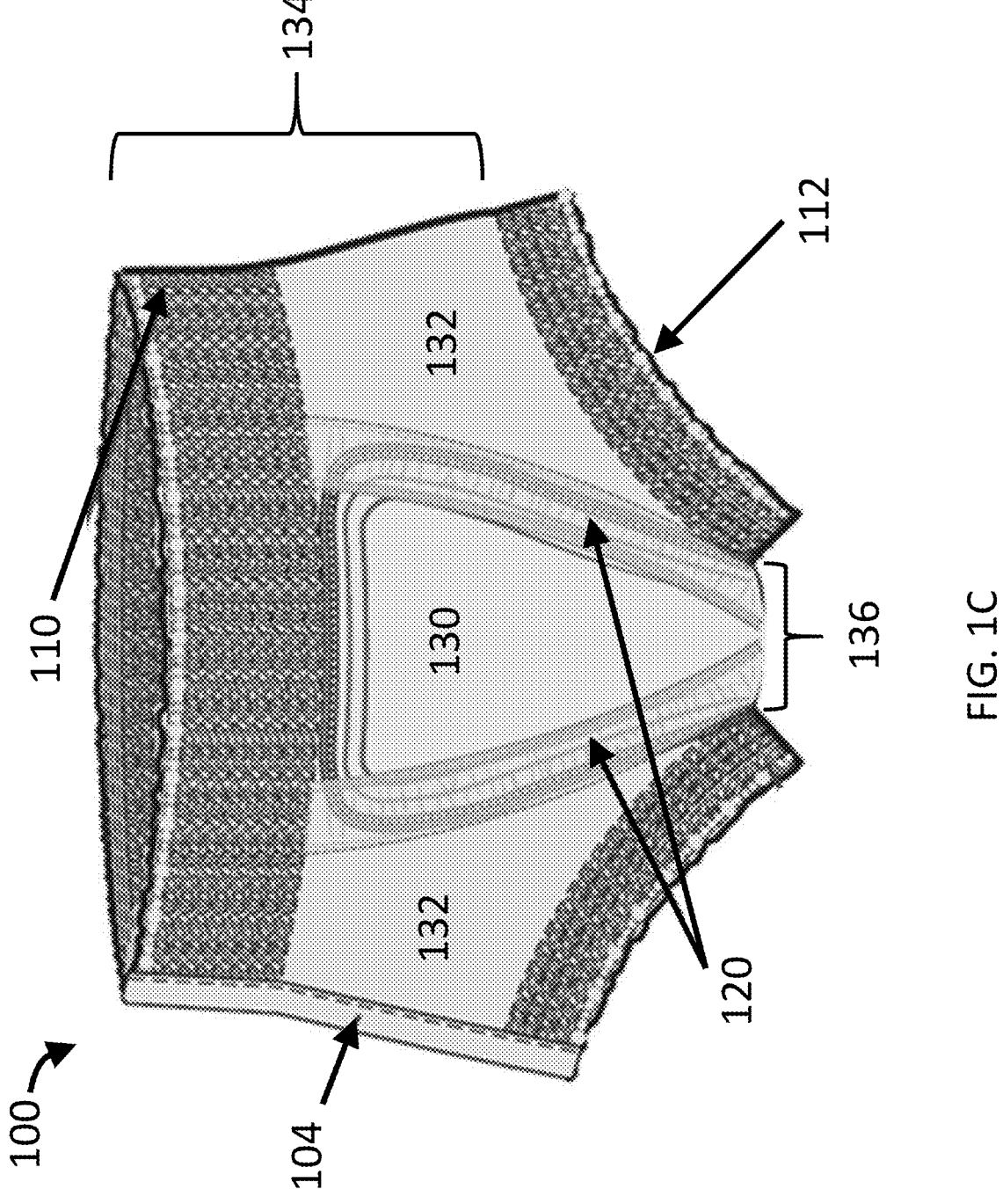
FIGS. 1C and 1D illustrate front and back views, respectively, of the inner layer of an example swim brief, according to some embodiments.
Figure 1D:
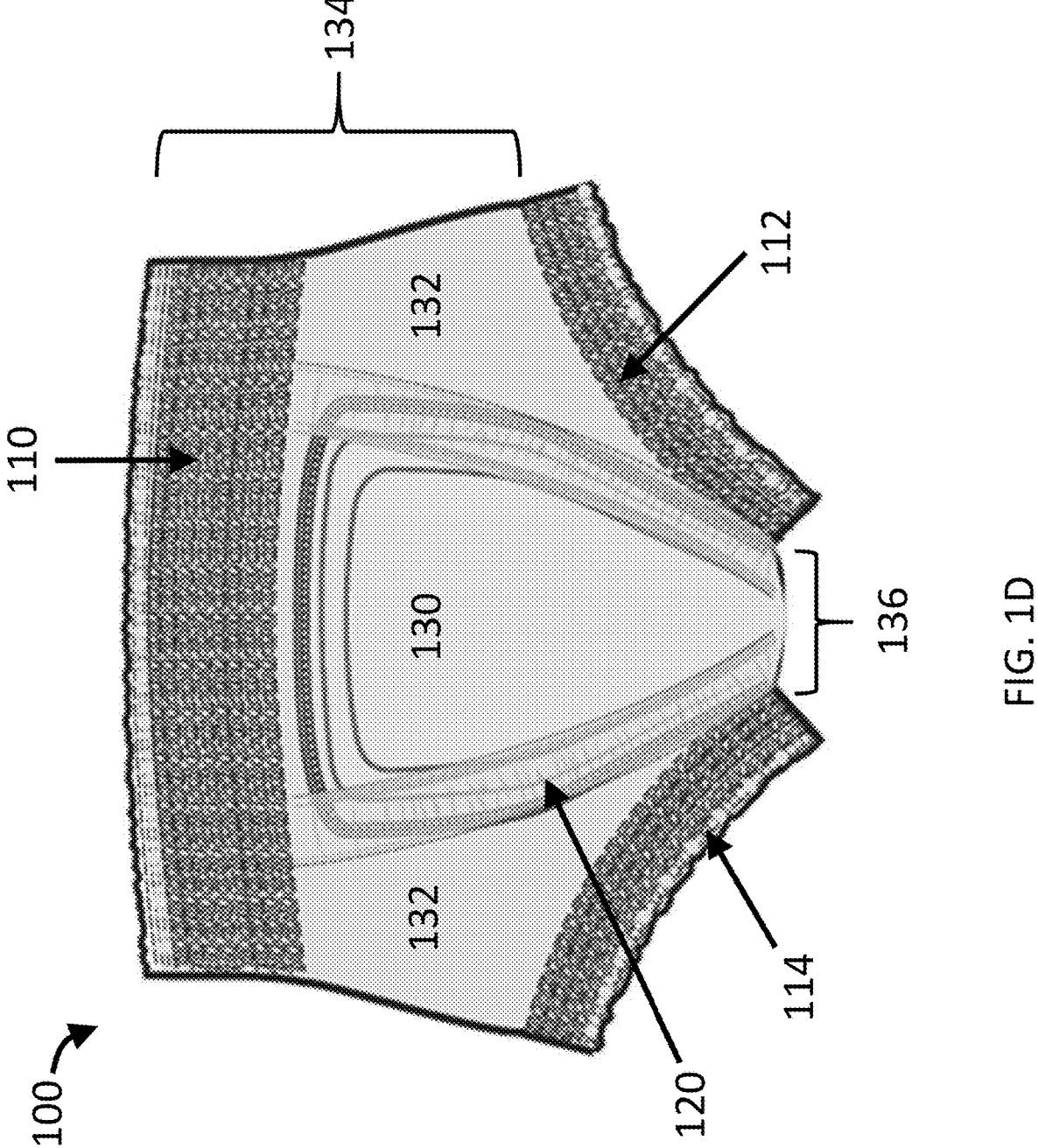

Additionally or alternatively, the torso portion of the swim brief 100 may comprise an inner layer. FIGS. 1C and 1D illustrate front and back views, respectively, of the inner layer of an example swim brief, according to some embodiments. The inner layer 132 may be located closest to the user's skin compared to the other layers of the swim brief 100. The inner layer 132 may extend from the torso receiving opening to both leg-receiving openings, including the front, back and side portions. In some embodiments, the inner layer 132 may cover the crotch portion 136. Alternatively, a containment insert 130 may cover the crotch portion, and edges of the inner layer 132 may attach to edges of the containment insert 130. In some embodiments, the inner layer may be adhered (e.g., sewn) at the edges of the torso-receiving band 110 and leg-receiving openings 112A and 112B. In some embodiments, the inner layer 132 may be formed from a plurality of portions (e.g., a front portion and a back portion) of fabric that are stitched together at one or more seams (e.g., crotch seam, side seams, back seam, front seam, etc.). In some embodiments, the inner layer 132 may comprise a breathable wick-away fabric including a knitted polyester fabric, a knitted hole fabric, rayon, tree cellulose, or a combination thereof, as non-limiting examples.

In some embodiments, the swim brief 100 may comprise one or more intermediate layers located between the inner layer and the outer layer. At least one of the intermediate layers may extend from the torso receiving opening to both leg-receiving openings, including wrapping around the crotch portion. In some embodiments, the intermediate layer may be attached to the inner layer 132 along one or more edges of the intermediate layer, such as along lateral edges of the intermediate layer. In some embodiments, the intermediate layer may be attached using a plurality of stitch lines. For example, the plurality of stitch lines may penetrate through the intermediate layer(s) and inner layer.

The swim brief 100 includes a containment insert 130 and sidewall barriers 120 for containing human waste such that it is located within the crotch portion 136. The containment insert 130 may be attached to one or more layers of the swim brief 100, such as the inner layer 132. In some embodiments, the containment insert 130 may be attached using a single needle topstitch formed along the edges of the containment insert 130. The sidewall barriers 120 may comprise a single layer of one or more of: a perforated mesh fabric, a knitted hole fabric, rayon, tree cellulose, or a combination thereof, and may have two rows of elastic chainstitch smocking along its edges. The sidewall barriers 120 may surround the edges of the containment insert and be attached to the inner layer 132 of the swim brief (e.g., using a 2-needle coverstitch). Example containment inserts are discussed in more detail below.

The swim brief 100 can be removed or worn (temporarily secured to the user) by using a fastener 102 (shown in FIG. 1A). In some embodiments, the fastener 102 may be a zipper whose pull tab is located at the bottom end when open (the swim brief 100 can be removed) and at the top end of the swim brief 100 when closed (the swim brief 100 can be temporarily secured to the user). In some embodiments, the zipper may be a waterproof zipper. A waterproof zipper may comprise teeth located closer to the user's skin (when the swim garment is worn by the user), and a waterproof coating (e.g., rubber, PVC, etc.) that covers the teeth when the zipper is closed. In some embodiments, the zipper may be made a material that has high resistance to corrosion, such as plastic. The fastener 102 may be such that it can protect excreted human waste from leaking outside of the swim brief 100. In some embodiments, fastener 102 may protect against human waste that was not contained by the containment insert 130. In some embodiments, one or more of the layers of the swim brief 100 may be attached together at the fastener 102. Additionally or alternatively, the layer(s) may be attached to the fastener 102.

In some embodiments, the swim brief 100 may comprise a fastener guard 104 (shown in FIG. 1C), configured to be located between the fastener 102 and the user's skin when the fastener 102 is closed. The fastener guard 104 may prevent the fastener 102 from contacting the user's skin, avoiding or reducing friction between the two.

In some embodiments, the fastener 102 may be located on one side of the swim brief 100, and an interior safety stitch may be located on the other side. In some embodiments, fasteners 102 may be located on both sides of the swim garment. In some embodiments, the swim brief 100 may not include a fastener, but instead sets of interior safety stitch may be located on both sides of the swim garment 100, and the swim garment may be pulled up onto or pulled down from the user's torso when worn or removed, respectively.

The swim brief 100 may comprise a plurality of openings and elastic bands. The properties (e.g., materials, stitching, etc.) and locations of the openings and/or bands may help contain excreted human waste while the disclosed swimwear garments are worn. In some embodiments, one or more elastic bands may comprise a plurality of fabric layers and an elastic (e.g., ¼," ¾," or 1" elastic sewn in). For example, the torso-receiving elastic band 110 can comprise a portion of the inner layer 132 and a portion of the outer layer 138. The portion of the inner layer 132 may comprise a perforated mesh fabric, a knitted hole fabric, rayon, tree cellulose, or a combination thereof, and a portion of the outer layer 138 may comprise a swimwear fabric (e.g., 1-ply swimwear fabric). Similarly, the leg-receiving elastic bands 112A and 112B can comprise a portion of the inner layer 132 and a portion of the outer layer. In some embodiments, the torso-receiving elastic band 110 may be attached to the inner layer

132 and the outer layer 138 at the bottom edge of the torso-receiving elastic band. The elastic bands of the present disclosure may stretch with the other materials of the swim garment.

In some embodiments, the torso-receiving elastic band 110 and/or leg-receiving elastic bands 112A and 112B may comprise an edge with a plurality of rows of stitching. In some embodiments, the stitching may comprise thread formations ranging from 4-7 rows. For example, the leg-receiving elastic bands 112A and 112B may comprise five rows of elastic chainstitch smocking that penetrates a plurality (e.g., all) of layers of the swim brief 100. As another example, the torso-receiving elastic band 110 may comprise seven rows of elastic chainstitch smocking. In some embodiments, the number of rows of stitching can be greater for the torso-receiving elastic band than for the leg-receiving elastic bands. A stitch seam may comprise an overlock edge to reduce or prevent loose threads. The overlock may be a 4-7 thread overlock used to hem the raw edges of the fabric. The stitching may include, but is not limited to, elastic chain stitch smocking through all layers of the swim garment. The elastic chain stitch smocking may allow the swim brief to be used for openings having all shapes and sizes. The elastic chain stitch may be created using a plurality of needles, increasing the strength of the seam and providing leak protection at the leg-receiving openings. Embodiments of the disclosure may comprise 3-7 rows of elastic chain stitch smocking.

In some embodiments, one or more (e.g., all) of the elastic bands comprises a gripper 114 for minimizing gaps between the user's body and the swim brief 100 when worn. A gripper 114 may be, e.g., a silicon gripper that creates a secure fit to the user and prevents or reduces movement of the swim brief 100 relative to the user. A secure fit and reduced relative movement may help contain human waste, creating a resilient seal (leak protection) at user's waist and/or legs. Example grippers may include, but are not limited to, silicon grip tape, printed silicone, silicone gripper elastic, and silicon adhesive. The gripper 114 may be stitched, glued, or printed onto the elastic bands (e.g., elastic band 110, elastic band 112A, elastic band 112B, etc.) or one or more fabric layers. In some embodiments, one or more of the elastic bands comprise elastic chain stitch smocking to minimize gaps and create a secure fit to the user. In some embodiments, the elastic bands, e.g., torso-receiving elastic band and/or leg-receiving elastic bands may comprise an additional layer used to provide comfort to the user; such as a soft layer.

Figure 2A:
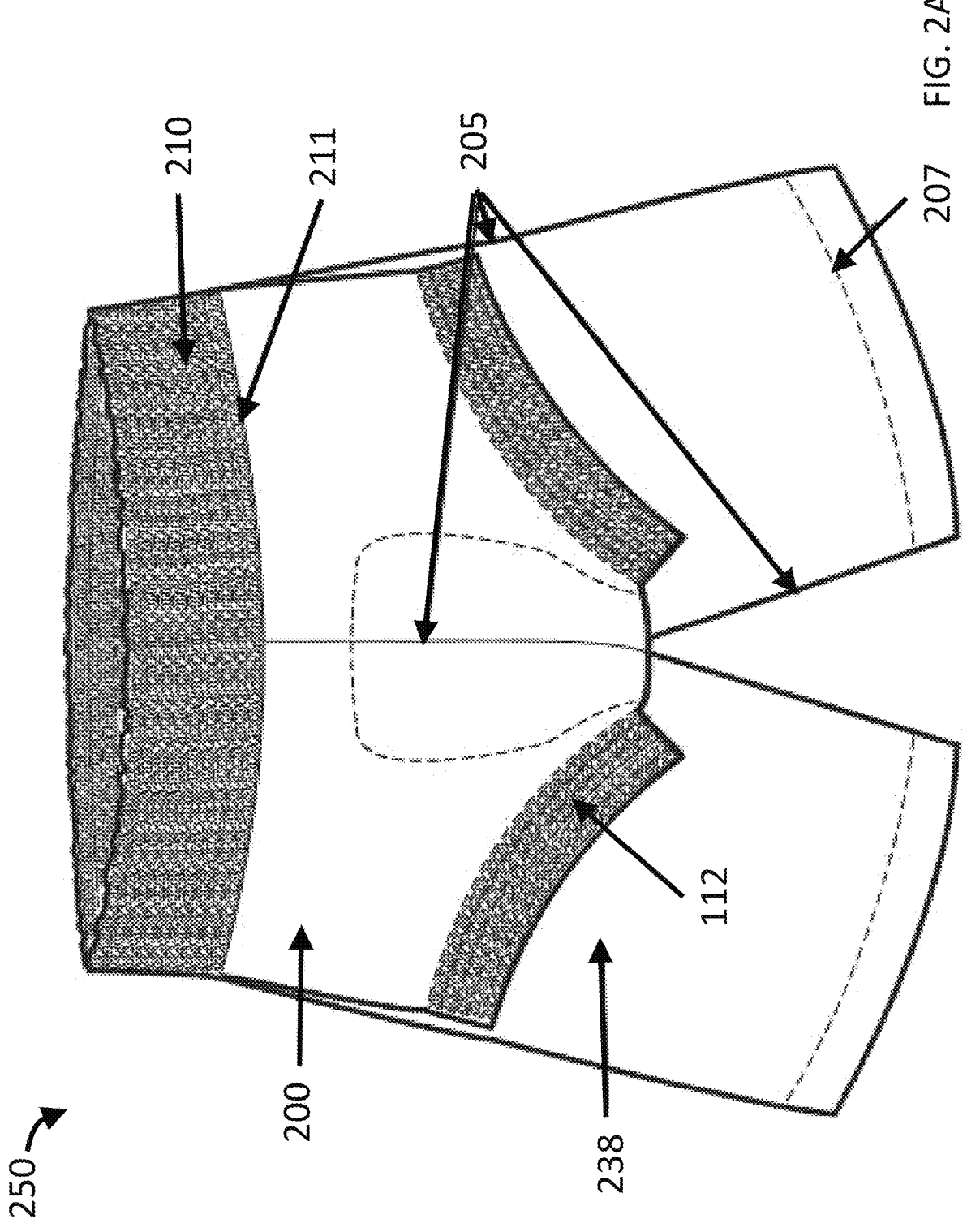
FIGS. 2A and 2B illustrate front and back views, respectively, of an example swim garment comprising a swim brief and a shell, according to some embodiments.
Figure 2B:
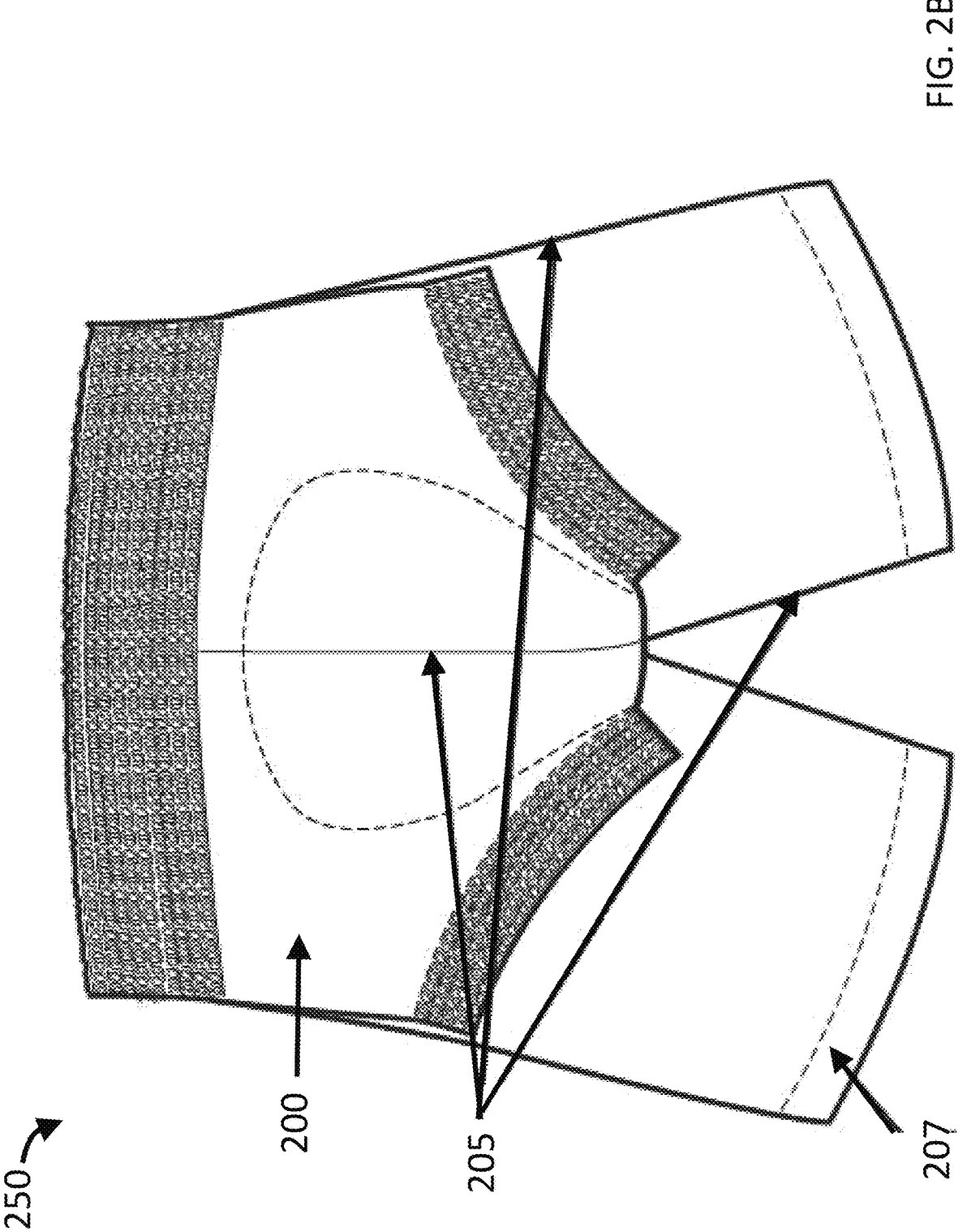

In some embodiments, the swim brief may be attached to one or more pieces to form a swim garment. As one non-limiting example, a swim garment may comprise a shell. FIGS. 2A and 2B illustrate front and back views, respectively, of an example swim garment 250 comprising a swim brief 200 and a shell 238, according to some embodiments. The swim brief 200 may have one or more properties similar to swim brief 100 of FIGS. 1A-1D. The shell 238 may have one or more properties similar to the outer layer, as described herein. For example, the shell 238 may comprise 1-ply swimwear fabric. The shell 238 may be a half-body shell, for example. In some embodiments, the shell 238 may comprise an outer layer, and the swim brief 200 may not include an outer layer and may be comprised of a containment insert and an inner layer. Alternatively, both the shell 238 and swim brief 200 may comprise outer layers, and the swim brief 200 may additionally comprise a containment insert and an inner layer.

The bottom portion of the shell 238 may extend past the leg-receiving elastic bands of the swim brief 200. For example, the shell 238 may attach only to the torso-receiving elastic band 210 and hang loosely, causing the swim garment 250 to have the protection mechanisms disclosed herein while appearing as boxer-type or shorts-type swim trunks, skirt-type swim bottoms, or the like.

The swim garment 250 may comprise an elastic band 210 located at the torso-receiving opening. The shell 238 may attach to the swim brief 300 at the elastic band 210, such as at the bottom 211 of the elastic band 210. The torso-receiving elastic band 210 may have one or more properties similar to the torso-receiving elastic band 110 (of FIGS. 1A-1D). For example, the torso-receiving elastic band 210 may comprise seven rows of elastic chainstitch smocking with a ¼" elastic inserted into the top edge seam allowance. The seam allowance may be finished in between layers of the elastic band 210. In some embodiments, the shell 238 may temporarily attach to the swim brief 300 and may be removed. For example, the shell 238 may comprise a decorative print, and the user may use a fastener, such as a zipper, that runs along the torso-receiving opening to temporarily attach or remove the shell 238 from the swim garment 250.

The shell 238 may comprise a plurality of seams 205, such as inseams, outseams, and front and/or back rise seams. The seams 205 may be clean finished with interior 5-thread safety stitch. Additionally or alternatively, the shell 238 may comprise a leg opening 207 that is finished with a turn back hem and single-needle topstitch.

Figure 3A:
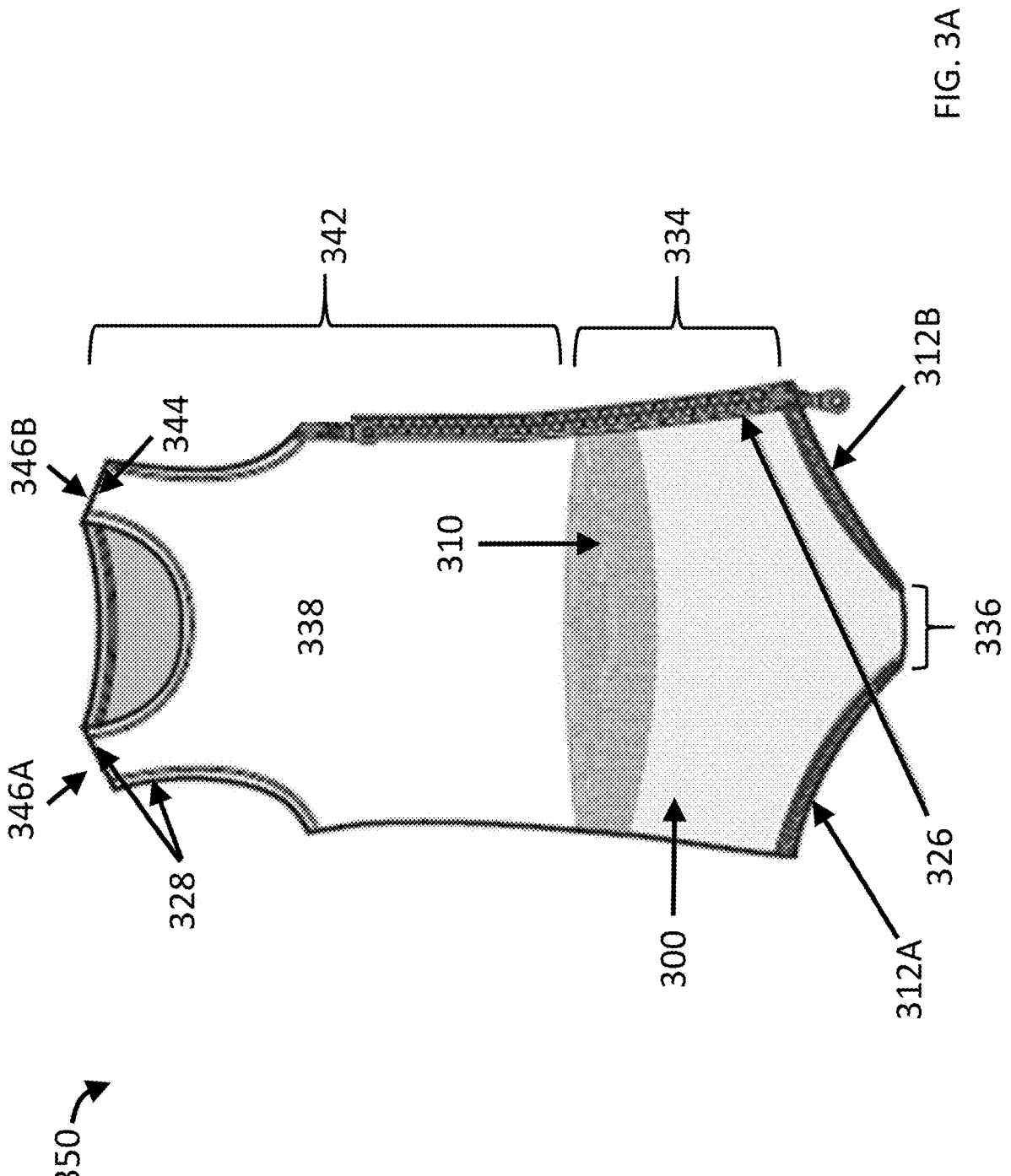
FIGS. 3A and 3B illustrate front and back views, respectively, of an example swim garment, according to some embodiments.
Figure 3B:
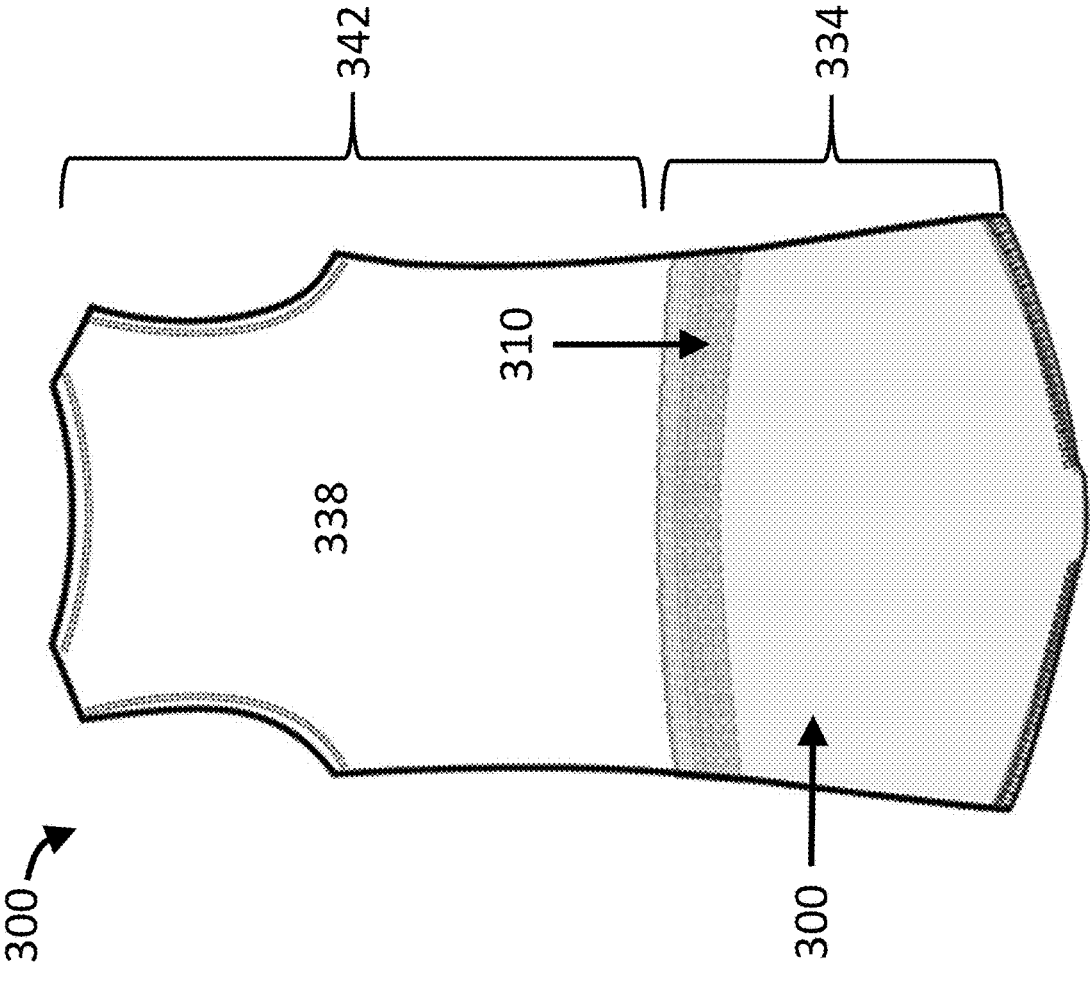

Embodiments of the disclosure may include a swim garment that covers the user's bottom body part (e.g., crotch, buttons) and other non-bottom body parts (e.g., the user's chest, shoulders, back, etc.). FIGS. 3A and 3B illustrate front and back views, respectively, of an example swim garment, according to some embodiments. These figures illustrate a swim garment 350 comprising a full-body shell. Swim garment 350 may comprise a lower portion 334 with an elastic band 310 located in the middle of swim garment 350 and elastic bands 312A and 312B located at the bottom end. In some embodiments, the elastic band 310 may be part of the swim brief 300. The swim brief 300 (shown in more detail in the front and back views of FIGS. 3C and 3D) may attach to the shell 338 at one or more locations, such as at the elastic band 310. The shell 338 may extend above the torso-receiving elastic band 310. Each elastic band 312A or 312B may form a leg-receiving opening. The swim garment 350 may comprise a crotch portion 336 located between the leg-receiving elastic bands 312A and 312B. The swim garment 350 may also comprise an upper portion 342. The upper portion 342 may comprise straps 346A and 346B located at the top end and the elastic band 310 located in the middle of swim garment 350. Each strap 346A or 346B may form an arm-receiving opening, and both straps together may form a neck-receiving opening.

The swim garment 350 may comprise a swim brief 300, which may be removable or permanently attached to the shell 338. For example, the swim brief 300 may be permanently attached to the inner layer of the shell 338 using a bar tack or the like. In some aspects, one or more sets of stitches may be added at the interface between the swim brief 300 and the inner layer of the shell 338 to provide reinforcement. The attachment mechanism (e.g., stitching, bar tack, a fastener, etc.) may be located in areas subject to stress and wear. For example, an attachment mechanism may be located along one or more edges of one or more elastic bands (e.g., elastic band 310 located in the middle of the swim garment 350, elastic bands 312A and 312B located at the leg-receiving openings, etc.).

The shell 338 may comprise one or more layers, such as an outer layer, one or more intermediate layers, an inner layer, or a combination thereof. One or more properties of the shell 338 may be substantially similar to the properties of a swim brief (e.g., swim brief 100 of FIGS. 1A-1D, swim brief 200 of FIGS. 2A and 2B). In some embodiments, the shell 338 may comprise a single layer similar to the outer layer of the swim brief. In some embodiments, one or more layers (e.g., the outer layer) of the shell 338 may continuously extend from the neck-receiving opening to the arm-receiving openings and the leg-receiving openings. Alternatively, one or more layers (e.g., the outer layer) of the shell 338 may extend from the neck-receiving opening to the arm-receiving openings and the elastic band 310 of the swim brief 300. For example, the shell 338 may be sleeveless or comprise short sleeves, ¾ sleeves, or long sleeves. Additionally or alternatively, the shell 338 may comprise brief bottoms, shorts, capris, or pants. In some embodiments, the shell 338 may be formed from a plurality of portions (e.g., a front portion and a back portion) of fabric that are stitched together at one or more seams (e.g., crotch seam, side seams, back seam, front seam, etc.). In some embodiments, the shell 338 may be separate from the swim brief 300, and the user may wear the shell 338 over the swim brief 300.

One or more openings (e.g., arm-receiving openings, neck-receiving opening, torso-receiving opening, and/or leg-receiving openings) may be formed by stitching one or more layers of the shell 338. One non-limiting example stitching may comprise a 2-needle coverstitch. In some embodiments, the opening(s) may be formed by using a clean finish with self-binding wrapping over the edges. The edges of the seam allowance of the opening(s) may be turned back ⅛"-¼", turned under, and stitched close to the folded edge using a straight stitch, thereby creating a neat, clean finish that will not ravel. In some embodiments, the stitches may be stretched, allowing the user to move freely with a wide range of motion.

The straps 346A and 346B may be located along the user's shoulders, such as between the user's neck and arms, when the swim garment 350 is worn. The torso-receiving elastic band 310 may be located proximate to the user's belly button (e.g., covering the user's lower torso) when the swim garment 350 is worn. The leg-receiving bands 312A and 312B may be located at the top of the user's legs when the swim garment 350 is worn. When worn, the front portion of the swim garment 350 is configured to cover the user's chest and a part of the waist, the back portion is configured to cover the user's back and buttocks, and the side portions are configured to cover the user's sides and hips.

The swim garment 350 can be removed or worn (temporarily secured to the user) by using one or more fasteners 326 and/or 344. In some embodiments, the fastener 326 may be a zipper whose pull tab is located at the bottom end when open (the swim garment 350 can be removed) and at the top end of the swim garment 350 when closed (the swim garment 350 can be temporarily secured to the user). In some embodiments, the zipper may be a double-ended zipper whose pull tabs are located at both the top end and bottom end when closed (the swim garment 350 cannot be removed). When the swim garment 350 is removable, the pull tabs may be located at the top end and middle end, middle end and bottom end, both at the top end, or both at the bottom end. The fasteners 344 may include, but not is limited to, snaps located on one or more straps 346. The fasteners 344 may include 1-4 snaps that allow the user to secure or remove the swim garment to the user's shoulders. For example, 2 ring snaps may be located at strap 346B, which may be located on the same side as the fastener 326.

Figure 3C:
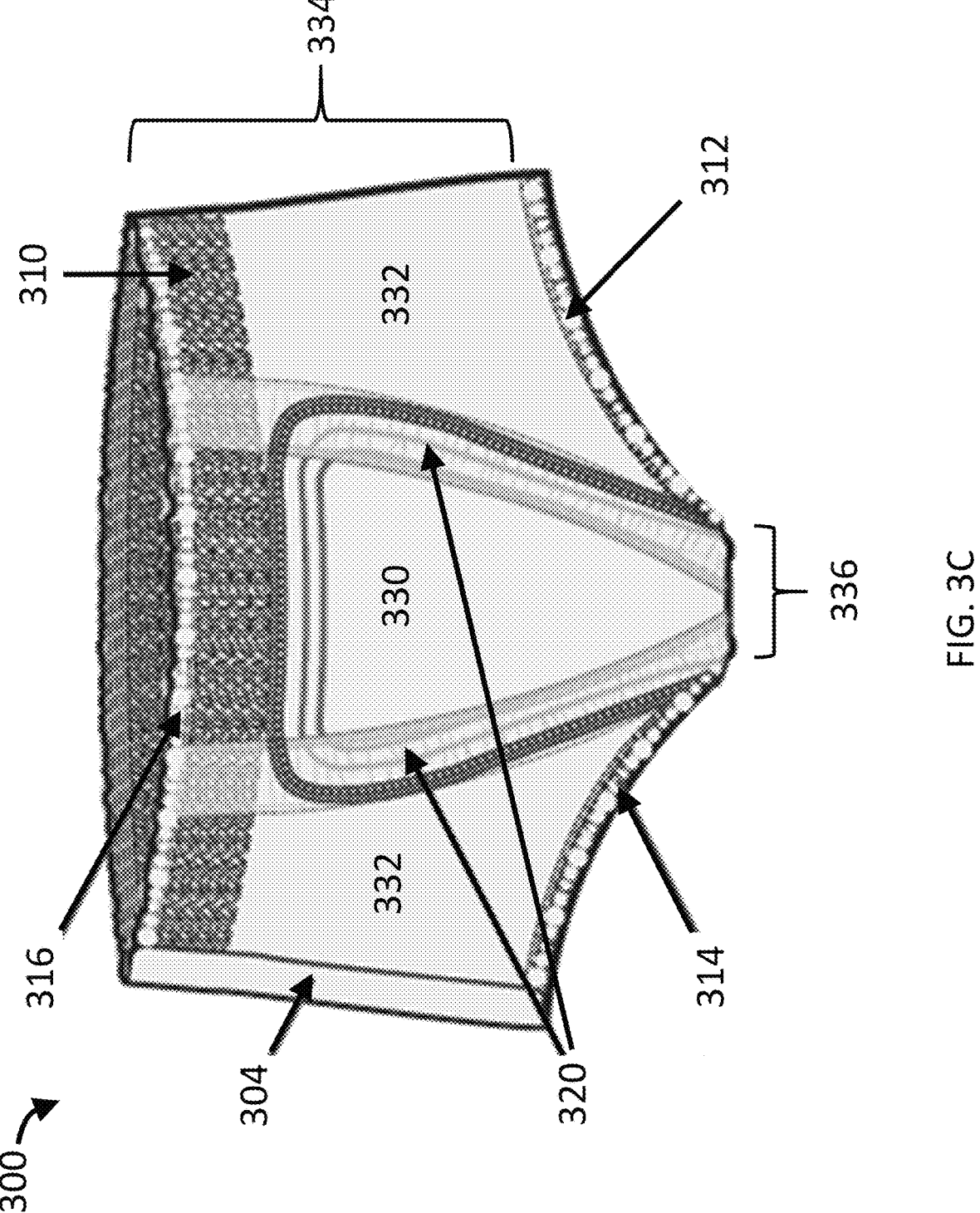
FIGS. 3C and 3D illustrate front and back views, respectively, of an example swim brief, according to some embodiments.
Figure 3D:
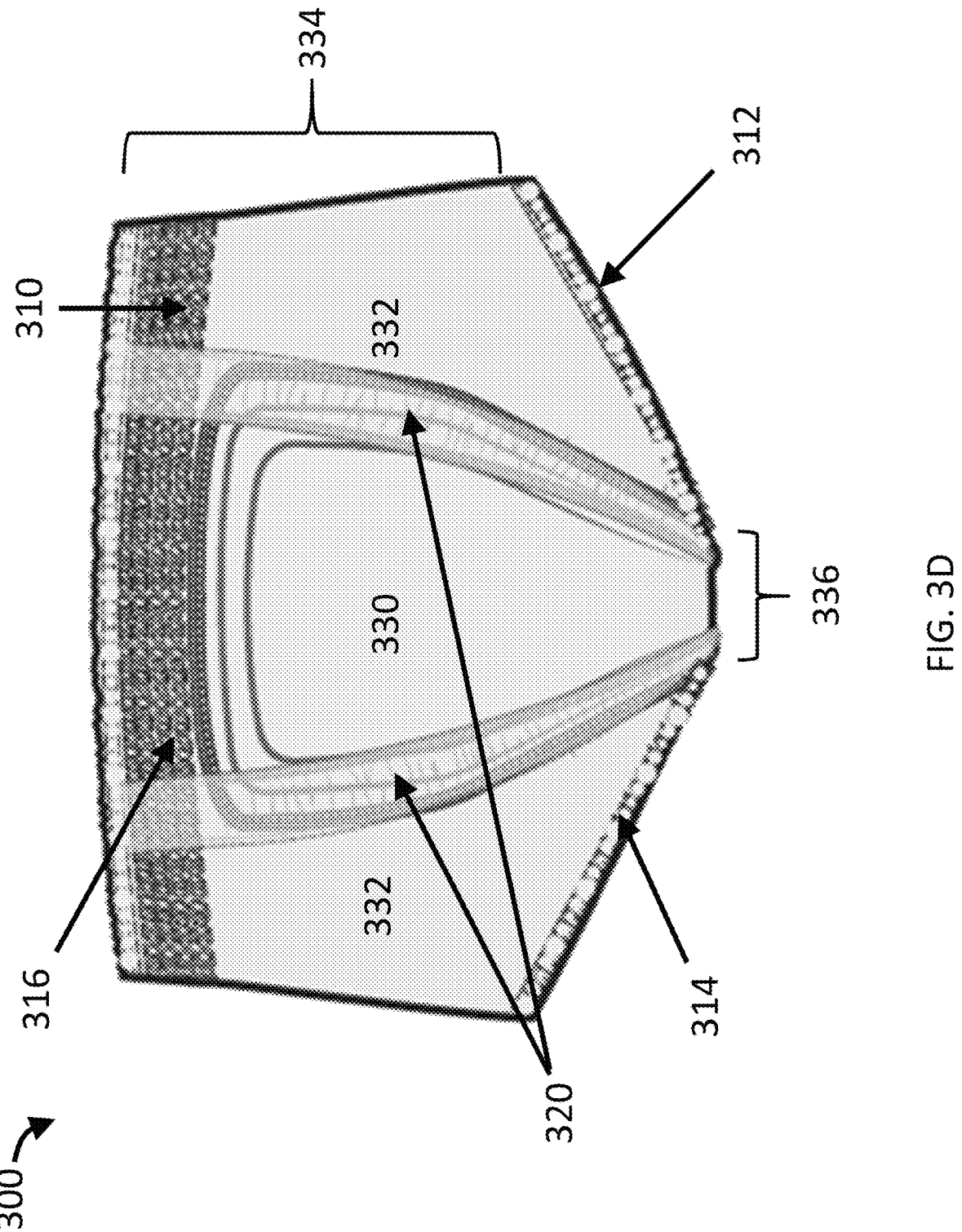

In some embodiments, at least the bottom portion 334 of the swim garment 350 may comprise an interior fastener panel 304, as shown in FIG. 3C. The interior fastener panel 304 may be configured to be located between the fastener 326 and the user's skin when the fastener 326 is closed. The interior fastener panel 304 may prevent the fastener 326 from contacting the user's skin, avoiding or reducing friction between the two. Embodiments of the disclosure may comprise the top portion 342 comprising an interior fastener panel.

Additionally or alternatively, the swim brief 300 may comprise a gripper 314 and/or gripper 316, which may be silicon grippers that creates a secure fit to the user and prevents or reduces movement of the swim brief 300 relative to the user. The swim brief 300 may also have an adjustable waistline with fasteners in order to create a customized fit. The swim brief 300 may also comprise an inner layer 332 and a containment insert 330 having one or more properties similar to the inner layer 132 and/or containment insert 130, respectively, disclosed herein. Embodiments of the disclosure may further include barriers 320, which help provide an additional layer of protection, further containing any human waste at the perimeter of the containment insert 130.

Embodiments of the disclosure may comprise a swim garment may have other configurations not shown in the figure, such as a garment comprising sleeves, a garment comprising leggings, or the like. The different configurations may include any of the properties or components disclosed herein and not alter the functions of the swim garment.

Figure 4A:
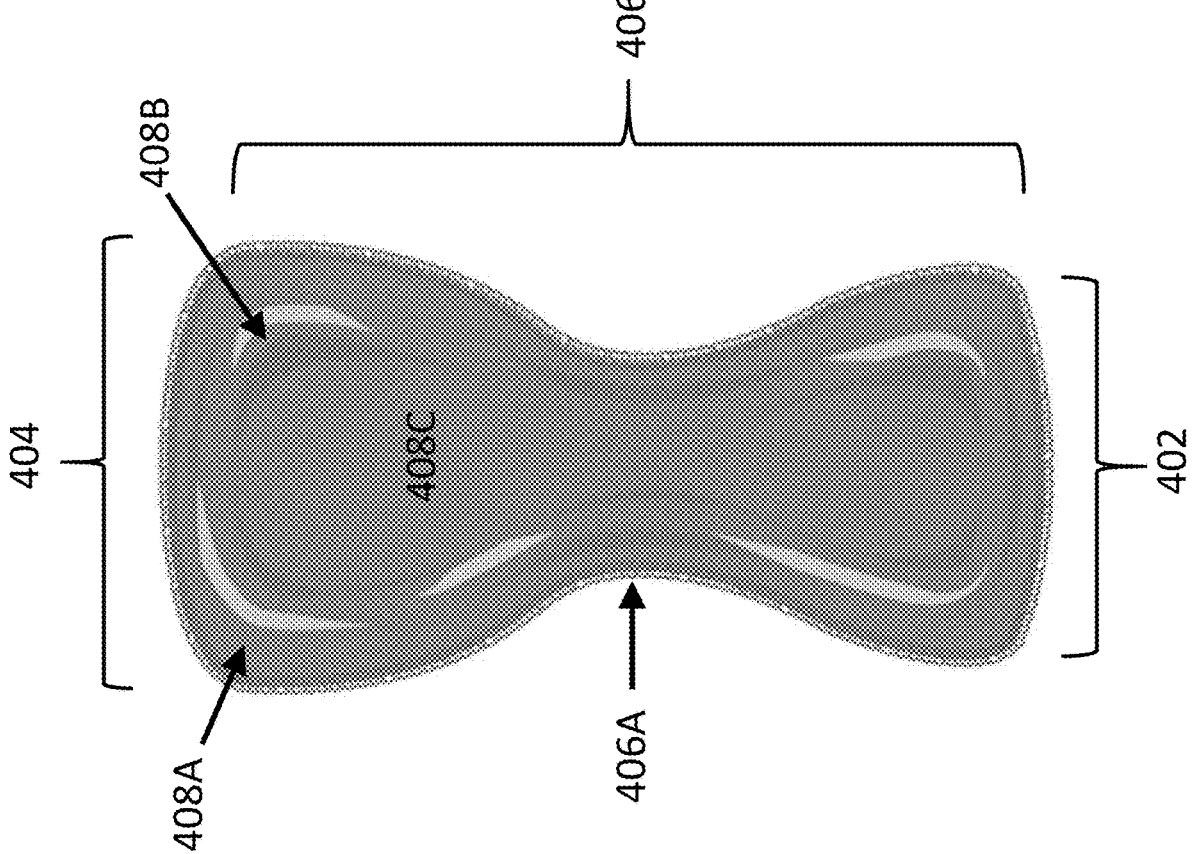
FIG. 4A illustrates a top view of an example containment insert, according to some embodiments.
Figure 4A:

FIG. 4A illustrates a top view of an example containment insert, according to some embodiments. The containment insert 430 may have a front portion 402, a back portion 404, side portions 406, outer portion 408A, elevated portion 408B, and an inner portion 408C. The front portion 402 may be configured to cover the user's crotch, and the back portion 404 may be configured to cover a portion of the user's buttocks. In some embodiments, the width of the front portion 402 may be less than the width of the back portion 404. The side portions 406 may include a plurality of contours, including 406A configured to follow the contours of the user's legs when wearing a swim brief or swim garment. The outer portion 408A may be located at the peripheral edges of the containment insert 430. The elevated portion 408B may be located adjacent to the outer portion 408A, closer to the inner portion 408C. In some embodiments, the elevated portion 408B may follow the outline of the outer portion 408A.

Figure 4B:
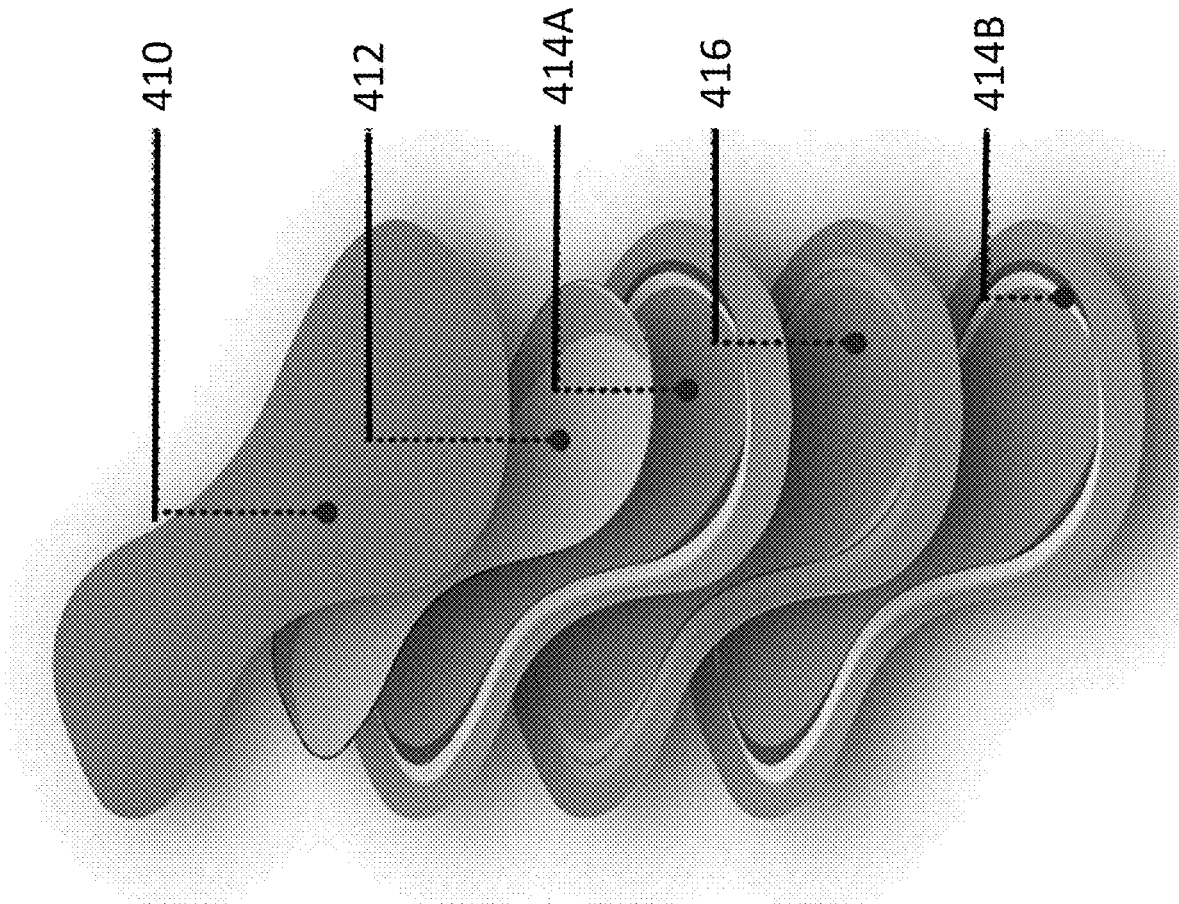
FIG. 4B illustrates the layers of an example containment insert, according to some embodiments.

The containment insert 430 may comprise a plurality of layers, as illustrated in the plan view of FIG. 4B. For ease with viewing the layers, the figure illustrates the plurality of layers as being separated, however, the layers may contact one another when the containment insert 430 is formed. The plurality of layers may comprise one or more filter layers 410, one or more absorbent layers 412, one or more waterproof layers 414, and one or more confinement layers 416. Embodiments of the disclosure may comprise the ordered arrangement of the layers as shown in the figure: the filter layer 410 located on one side of the absorbent layer 412, the absorbent layer 412 located between the filter layer 410 and the waterproof layer 414A, the waterproof layer 414A located between the absorbent layer 412 and the confinement layer 416, and the waterproof layer 414B located on one side of the confinement layer 416. Embodiments of the disclosure may include different orders among the layers. Embodiments of the disclosure may also include layers with deodorizing elements to neutralize odors. Embodiments of the disclose may also be adapted for use in environments other than swimwear, including, but not limited to, diapers, pads, or other waste-containment garments. Embodiments of the disclosure may also include a containment insert 430 with an adhesive backing for secure attachment.

The filter layer(s) 410 may filter out one or more types of human waste (preventing or reducing penetration to other layers of the containment insert 430), while allowing other types of human waste (e.g., liquid human waste) to pass through to the other layers of the containment insert 430. For example, the filter layer 410 may catch solids such as feces (a first type of human waste), but may allow urine to pass through. The filter layer 410 may extend from the front portion 402, back portion 404, and side portions 406 (e.g., the lateral entirety of the containment insert 430). In some embodiments, the filter layer 410 may comprise a perforated mesh fabric, a knitted hole fabric, rayon, tree cellulose, or a combination thereof. In some embodiments, the filter layer 410 may comprise a soft fabric with antibacterial treatment.

The absorbent layer 412 may absorb one or more liquids, such as urine (a second type of human waste) that the filter layer 410 allowed to pass through. The absorbent layer 412 may be located at the inner portion 408C. As discussed in more detail below, the containment insert 430 may comprise one or more valley-like features, where the inner portion 408C is located at the lower portions of the valley. In some embodiments, the absorbent layer 412 may be located at these lower portions. In some embodiments, the absorbent layer 412 may comprise a French or Looped terry fabric, cellulose, or a combination thereof. In some embodiments, the absorbent layer 412 may comprise a hydrophilic foam or fabric, which, in some embodiments, may have a reticulated open cell structure. In some embodiments, there may be an adhesive over the absorbent layer 412 to ensure lamination between the filter layer(s) 410 and the other layers.

The waterproof layer 414A may be configured to prevent or reduce human waste penetrating through and reaching the confinement layer 416. Additionally or alternatively, the waterproof layer 414A may be configured to prevent or reduce liquids of the swimming environment from reaching the filter layer 410 and/or the absorbent layer 412. In some embodiments, the waterproof layer 412A may comprise a coated nylon or a polyurethane film fabric.

The confinement layer 416 may comprise one or more materials capable of creating one or more features for confining human waste. For example, the confinement layer 416 may comprise a hydrophobic foam or fabric including, but not limited to, polyethenum, polyurethane, ethylene vinyl acetate, and styrene butadiene rubber. The confinement layer 416 may, in some embodiments, comprise a hydrophobic foam or fabric with a reticulated open cell structure. The confinement layer 416 may be carved in order to create a hollow effect in the waste spots to prevent solid evacuations.

Figure 4C:
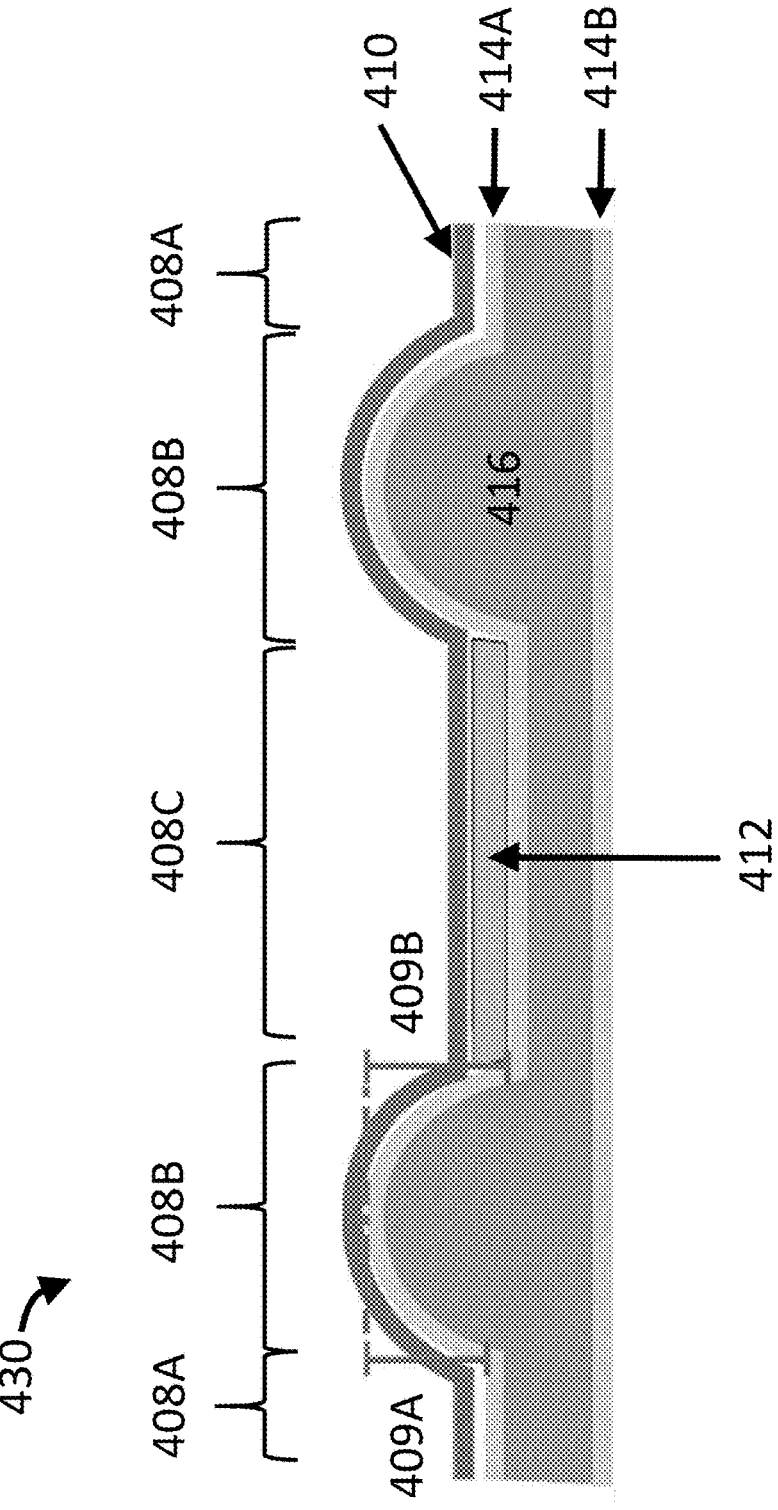
FIG. 4C illustrates a cross-sectional view of an example containment insert, according to embodiments of the disclosure.

The confinement layer 416 may comprise one or more features to confine human waste. One non-limiting example feature is a valley formed from one or more elevated portions surrounding an inner portion, where the confinement layer at the inner portion is thinner than the confinement layer at the elevated portion(s). FIG. 4C illustrates a cross-sectional view of an example containment insert 430, according to embodiments of the disclosure. The containment insert 430 may comprise a plurality of portions, such as an outer portion 408A, an elevated portion 408B, and an inner portion 408C. The confinement layer 416 may have a plurality of thicknesses and shapes for different portions of the containment insert 430. For example, the confinement layer 416 at the outer portion 408A may be thicker than the confinement layer 416 at the inner portion 408C. The confinement layer 416 may be thicker at the elevated portion 408B (compared to the outer portion 408A and the inner portion 408C), creating this valley-like feature that helps contain human waste within the center portion 408C. The one or more features of the containment layer may be located in the elevated portion 408B. In some embodiments, the thickness difference measured from the top of the valley-like feature to its lower portions may be different for the outer portion 408A and the inner portion 408C. For example, the distance 409A between the top of the feature to the confinement layer 416 at the outer portion 408A may be less than the distance 409B between the top of the feature to the confinement layer 416 at the inner portion 408C. That is, the confinement layer 416 at the outer portion 408A may be thicker than the confinement layer 416 at the inner portion 408C. As one non-limiting example, distance 409A may be 5 mm, and distance 409B may be 8 mm. In some embodiments, the thickness at the inner portion 408C may be between 4-8 mm, elevated portion 408B may be between 10-15 mm, and/or the outer portion 408A may be between 2-5 mm.

In some embodiments, the inner portion 408C may not comprise confinement layer 416. The inner portion may comprise a filter layer 410, an absorbent layer 412, and waterproof layers 414A and 414B. The layers of the inner portion 408C may be stitched together at the interface between the inner portion 408C and the elevated portion 408B.

In some embodiments, the thicknesses of the filter layer 410 and waterproof layers 414A and 414B may be the same throughout the outer portion 408A, elevated portion 408B, and inner portion 408C of the containment insert 430. The filter layer 410 and waterproof layer 414A may not be flat and may follow the contours of the confinement layer 416 and/or absorbent layer 412.

Referring back to FIG. 4B, the containment insert 430 may comprise a waterproof layer 412B. The waterproof layer 412B may be configured to prevent or reduce liquids of the swimming environment from reaching the other layers of the containment insert 430. Additionally or alternatively, the waterproof layer 412B may be configured to prevent or reduce human waste from leaving the swim brief or garment and reaching the water of the swimming environment. In some embodiments, the waterproof layer 412B may comprise a polyurethane film fabric or a coated nylon fabric such as thermoplastic polyurethane (TPU), polyurethane laminate (PUL), extra-long staple (ELS cotton), neoprene, rubber, or the like.

When attached to a swim brief, the filter layer 410 shown in the figure may be configured to contact the user's body or an inner layer of the swim garment. Additionally or alternatively, the waterproof layer 414B may be configured to contact the liquids of the swimming facility (e.g., water) or an outer layer of the swim garment.

Although discussed in the context of a swim brief and swim garment, the containment insert disclosed herein can be used for non-swimming applications, such as everyday use, cycling, or the like.

Although examples of this disclosure have been fully described with reference to the accompanying drawings, it is to be noted that various changes and modifications will become apparent to those skilled in the art. Such changes and modifications are to be understood as being included within the scope of examples of this disclosure as defined by the appended claims.

The invention claimed is:

1. A containment insert for containing excreted human waste, the containment insert comprising:
   a filter layer that filters out solid human waste;
   a confinement layer comprising one or more features for confining the solid human waste, wherein the one or more features comprise a valley formed from one or more elevated portions surrounding an inner portion, wherein the confinement layer at the inner portion is thinner than the confinement layer at the one or more elevated portions, wherein an outer portion surrounds the one or more elevated portions;
   an absorbent layer that absorbs liquid human waste, wherein the absorbent layer is located at the inner portion of the confinement layer between the one or more elevated portions; and
   one or more waterproof layers that prevent or reduce liquids from penetrating through the containment insert,
   wherein the containment insert is configured for integration into a reusable swim brief.

2. The containment insert of claim 1, further comprising:
   an outer portion having a thickness between 2 mm and 5 mm;
   an elevated portion having a thickness between 10 mm and 15 mm; and
   an inner portion having a thickness between 4 mm and 8 mm.

3. The containment insert of claim 1, further comprising:
   a front portion and a back portion, wherein a width of the front portion is less than a width of a back portion.

4. The containment insert of claim 1, wherein the filter layer is located on one side of the absorbent layer, wherein the absorbent layer is positioned between the filter layer and at least one of the one or more waterproof layers;
   wherein at least one of the one or more waterproof layers is located between the absorbent layer and the confinement layer, and another waterproof layer of the one or more waterproof layers is located on one side of the confinement layer;
   wherein the confinement layer comprises a foam fabric.

5. The containment insert of claim 1,
   wherein the reusable swim brief comprises an outer layer and an inner layer covering front, back, and side portions of the reusable swim brief,
   wherein the confinement layer at an outer portion of the containment insert is thicker than the confinement layer at an inner portion of the containment insert.

6. The containment insert of claim 1, wherein the confinement layer comprises a resilient foam fabric with properties that reduce moisture absorption and containment, providing improved performance in managing excreted human waste.

7. The containment insert of claim 1, wherein a thickness of at least one of the one or more waterproof layers is constant throughout an outer portion, an elevated inner portion, and an inner portion of the containment insert.

8. The containment insert of claim 1, wherein the reusable swim brief comprises an outer layer and an inner layer and one or more of: the outer layer or the inner layer cover a crotch portion of the reusable swim brief.

9. The containment insert of claim 1, wherein the reusable swim brief comprises an inner layer, the inner layer comprising a breathable wick-away fabric.

10. The containment insert of claim 1, wherein the reusable swim brief comprises an inner layer and sidewall barriers, the sidewall barriers surrounding edges of the containment insert and attached to the inner layer.

11. The containment insert of claim 1, wherein one or more of: a torso-receiving elastic band or leg-receiving elastic bands of the reusable swim brief comprise an inner layer of the reusable swim brief, an elastic band, and an outer layer of the reusable swim brief.

12. The containment insert of claim 1, wherein one or more of: a torso-receiving elastic band or leg-receiving elastic bands of the reusable swim brief comprise a plurality of rows of stitching.

13. The containment insert of claim 1, further comprising: a deodorizing element configured to neutralize odors.

14. The containment insert of claim 1, further comprising: a moisture-wicking layer located adjacent to the absorbent layer, the moisture-wicking layer configured to transport liquid away from the absorbent layer.

15. The containment insert of claim 1, wherein the one or more waterproof layers are impermeable to liquids while allowing airflow to maintain comfort.

16. The containment insert of claim 1, further comprising: an adhesive backing for secure attachment to an inner surface of a reusable swim brief.

17. A reusable swim brief comprising: a containment insert for containing excreted human waste, the containment insert comprising:

a filter layer that filters out solid human waste;

a confinement layer comprising one or more features for confining the solid human waste, wherein the one or more features comprise a valley formed from one or more elevated portions surrounding an inner portion, wherein the confinement layer at the inner portion is thinner than the confinement layer at the one or more elevated portions, wherein an outer portion surrounds the one or more elevated portions;

an absorbent layer that absorbs liquid human waste, wherein the absorbent layer is located at the inner portion of the confinement layer between the one or more elevated portions; and one or more waterproof layers that prevent or reduce liquids from penetrating through the containment insert,

1; and an adjustable waistband for a customizable fit, wherein the adjustable waistband includes one or more fasteners for easy removal and adjustment of the reusable swim brief.

18. The reusable swim brief of claim 17, further comprising:

leg-receiving elastic bands that create a secure seal around a user's legs.

19. The reusable swim brief of claim 17, wherein the swim brief is configured for use by users of any age.

\* \* \* \* \*